US006963772B2

(12) United States Patent
Bloom et al.

(10) Patent No.: US 6,963,772 B2
(45) Date of Patent: Nov. 8, 2005

(54) USER-RETAINABLE TEMPERATURE AND IMPEDANCE MONITORING METHODS AND DEVICES

(75) Inventors: Matthew Bloom, Palo Alto, CA (US); Wm. Leroy Heinrichs, Menlo Park, CA (US); Gregory T. A. Kovacs, Stanford, CA (US); David Salzberg, Mountin View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 101 days.

(21) Appl. No.: 10/125,051

(22) Filed: Apr. 17, 2002

(65) Prior Publication Data

US 2003/0199783 A1    Oct. 23, 2003

(51) Int. Cl.[7] ............................ A61B 5/053; A61B 5/00
(52) U.S. Cl. ....................................... 600/547; 600/549
(58) Field of Search ................................. 600/547, 548, 600/549, 300, 301

(56) References Cited

U.S. PATENT DOCUMENTS

| | | |
|---|---|---|
| 3,980,073 A | 9/1976 | Shaw, IV |
| 4,232,552 A | 11/1980 | Hof et al. |
| 4,300,574 A | 11/1981 | Briggs |
| 4,398,910 A | 8/1983 | Blake et al. |
| 4,465,481 A | 8/1984 | Blake |
| 4,692,153 A | 9/1987 | Berlin et al. |
| 4,805,621 A | 2/1989 | Heinze et al. |
| 4,837,501 A | 6/1989 | Fry et al. |
| 5,045,075 A | 9/1991 | Ersek |
| 5,068,618 A | 11/1991 | Fry et al. |
| 5,116,310 A | 5/1992 | Seder et al. |
| 5,181,905 A * | 1/1993 | Flam ........................ 600/549 |
| 5,211,479 A * | 5/1993 | Coffey et al. ............... 600/549 |
| 5,425,362 A * | 6/1995 | Siker et al. ................... 60/549 |
| 5,513,636 A | 5/1996 | Palti |
| 5,546,955 A * | 8/1996 | Wilk .......................... 600/549 |
| 5,588,958 A | 12/1996 | Cunningham et al. |
| 5,596,995 A | 1/1997 | Sherman et al. |
| 5,662,711 A | 9/1997 | Douglas |
| 5,697,911 A | 12/1997 | Yarger |
| 5,738,107 A | 4/1998 | Martinsen et al. |
| 5,807,270 A * | 9/1998 | Williams .................... 600/547 |
| 5,879,292 A | 3/1999 | Sternberg et al. |
| 5,968,024 A | 10/1999 | Freeman |
| 5,984,874 A * | 11/1999 | Cerwin ....................... 600/549 |

(Continued)

OTHER PUBLICATIONS

Stein, L.E., et al., A comparison steady state and transient thermography techniques using a healing tendon model Veterinary Surgery, 1988. 17(2): p. 90-6.

(Continued)

*Primary Examiner*—Eric F. Winakur
(74) *Attorney, Agent, or Firm*—Carol L. Francis; Bozicevic, Field & Francis LLP

(57) ABSTRACT

A user-retainable monitoring system is disclosed. At least a pair of sensors is provided in association with a support member. The support member is preferably of a type that may be worn by or at least temporarily implanted in a patient. Possible sensor types include temperature sensors and impedance sensors. Temperature sensors may be used to detect a temperature differential between areas of tissue indicative of pathology. Impedance sensors are used to detect subcutaneous fluid detection. The support member may take the form of a bandage, drain or other structure. Monitor structures as described may have stand-alone utility or be connected to a processor or data recorder to enable various functions.

41 Claims, 7 Drawing Sheets

U.S. PATENT DOCUMENTS

| | | |
|---|---|---|
| 6,083,174 A | 7/2000 | Brehmeier-Flick et al. |
| 6,099,513 A | 8/2000 | Spehalski |
| 6,135,968 A | 10/2000 | Brounstein |
| 2002/0026123 A1 | 2/2002 | Pearlman |

OTHER PUBLICATIONS

Viitanen, S.M. and J. Viljanto, *Wound healing. A thermographic study*. Annales Chirugiae et Gynaecologiae Fenniae, 1972. 61(2): p. 101-6.

Kliot, D.A. and S.J. Birnbaum, *Thermographic studies of wound healing*. American Journal of Obstetrics & Gynecology, 1965. 93(4): p. 515-21.

Horzic, M., D. Bunoza, and K. Maric, *Three-dimensional observation of wound temperature in primary healing*. Ostomy Wound Manage, 1996. 42(8): p. 38-40, 42-4, 46-7.

Horzic, M., D. Bunoza, and K. Maric, *Contact Thermography in a study of primary healing of surgical wounds*. Ostomy Wound Management, 1996. 42(1): p. 36-8.

Waterman, N.G., L. Goldberg, and T. Appel, *Tissue temperatures in localized pyogenic infections*. American Journal of Surgery, 1969. 118(1): p. 31-5.

Golbranson, F.L., E.G. Yu, and R.H. Gelberman, The use of skin temperature determinations in lower extremity amputation level selection. Foot & Ankle, 1982. 3(3): p. 170-2.

Stoner, H.B., L. Taylor, and R.W. Marcuson, The value of skin temperature measurements in forecasting the healing of a below-knee amputation for end-stage ischaemia of the leg in peripheral vascular disease. European Journal of Vascular Surgery, 1989. 3(4): p. 355-61.

Sandier, D.A. and J.F. Martin, Liquid crystal termography as a screening test for deep-vein thromobosis. Lancet, 1985. 1(8430): p. 665-7.

Gaiziunas, A.G. and M.H. Hast, *Temperature gradients and prediction of flap viability* . Journal of Otolaryngology, 1976. 5(5): p. 399-402.

Holmstrom, H., *Temperature changes of wound fluid inbipedicle tube flaps. An experimental study*. Scandinavian Journal of Plastic & Reconstructive Surgery, 1973. 7(2): p. 102-4.

Hackett, M.E., The use of thermography in the assessment of depth of burn and blood supply of flaps, with preliminary reports on its use in Dupuytren's contracture and treatment of varicose ulcers. Br J. Plast Surg, 1974. 27(4): p. 311-7.

Frank, S.M., et al., Temperature monitoring practices during regional anesthesia [see comments].Anesthesia & Analgesia, 1999. 88(2): p. 373-7.

Park, E.S., et al., Comparison of sympathetic skin response and digital infrared thermographic imaging in peripheral neuropathy. Yonsei Medical Journal, 1994. 35(4): p. 429-37.

Palmer, J.B., et al., *A cellist with arm pain: thermal asymmetry in scalenus anticus syndrome*. Archives of Physical Medicine & Rehabilitation, 1991. 72(3): p. 237-42.

Pogrel, M.A., C. McNeill, and J.M. Kim, The assessment of trapezius muscle symptoms of patients with temporomandibular disorders by the use of liquid crystal thermography. Oral Surgery, Oral Medicine, Oral Pathology, Oral Radiology, & Endodontics, 1996. 82(2): p. 145-51.

Robicsek, F., et al., *The application of thermography in the study of coronary blood flow*. Collected Works on Cariopulomary Disease, 1979. 22: p. 49-56.

Robicsek, F., et al., The value of thermography in the early diagnosis of postoperative sternal wound infections. Thoracic & Cardiovascular Surgeon, 1984. 32(4): p. 260-5.

Saxena, A.K., et al., *Thermography of Clostridium perfringens infection in childhood*. Pediatric Surgery International, 1999. 15(1): p. 75-6.

Cole, R.P., et al., Thermographic assessment of burns using a nonpermeable membrane as wound covering. Burns, 1991. 17(2): p. 117-22.

Ferguson, J.C. and C.J. Martin, *A study of skin temperatures, sweat rate and heat loss for burned patients*. Clinical Physics & Physiological Measurement, 1991. 12(4): p. 327-75.

Boylan, A., C.J. Martin, and G.G. Gardner, *Infrared emissivity of burn wounds*. Clinical Physics & Physiological Measurement, 1992. 13(2): p. 125-7.

Wyllie, F.J. and A.B. Sutherland, Measurement of surface temperature as an aid to the diagnosis of burn depth. Burns, 1991. 17(2): p. 123-7.

Mladick, R., N. Georgiade, and F. Thorne, *A clinical evaluation of the use of thermography in determining degree of burn injury*. Plastic & Reconstructive Surgery, 1966. 38(6): p. 512-8.

Lawson, R.W., G. Webster, D., *Thermographic Assessment of Burns and Frostbite*. Can. Med. Ass. J., 1961.84: p. 1129.

Yamagami, S. and H. Yamagami, *Direct measurement of wound temperature during phacoemulsification*. Ophthalmologica, 1998. 212(1): p. 50-2.

Yamarnoto, K. and S. Osako, Temperature and humidity in the surgical wound cavity following tympanaplasty. Jibinkoka, 1966. 38(11): p. 1165-9.

* cited by examiner

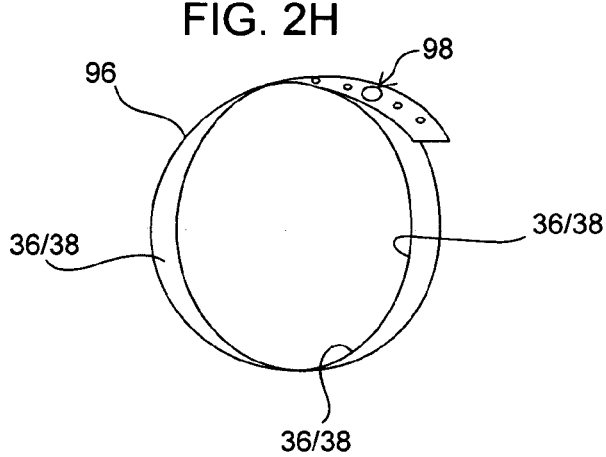
FIG. 2H
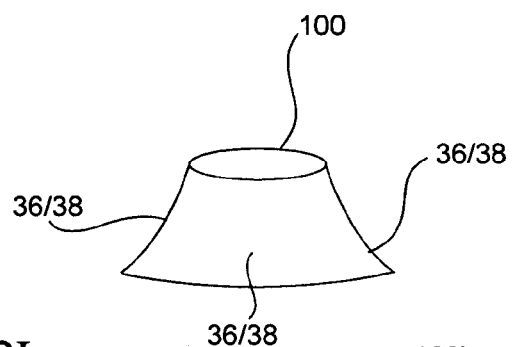
FIG. 2I
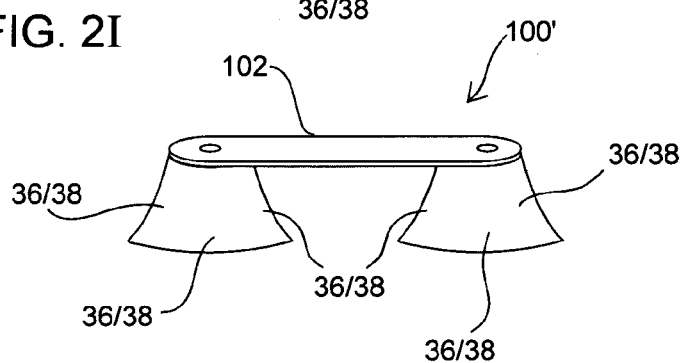
FIG. 2J
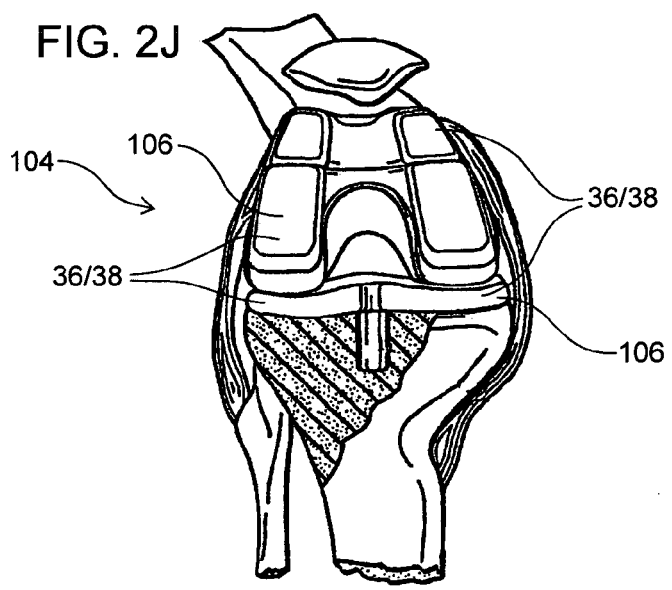

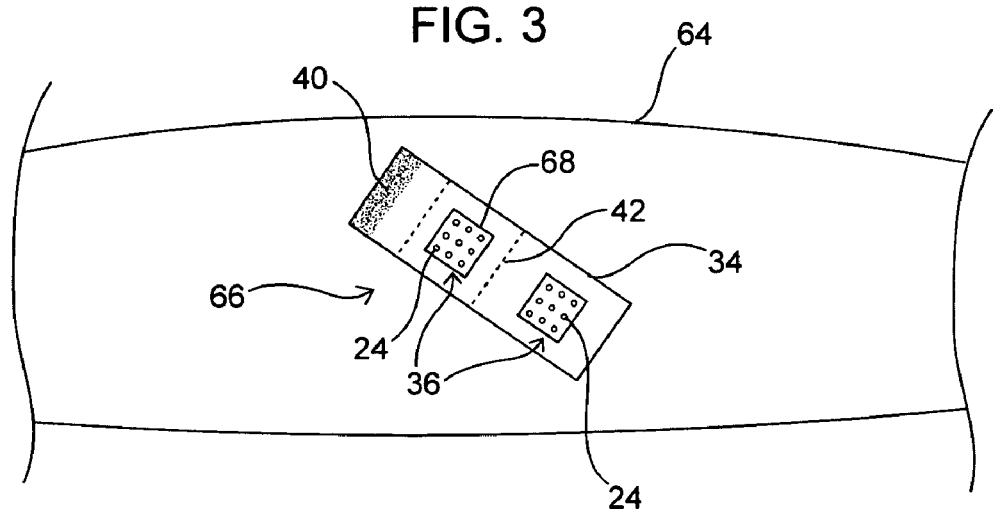
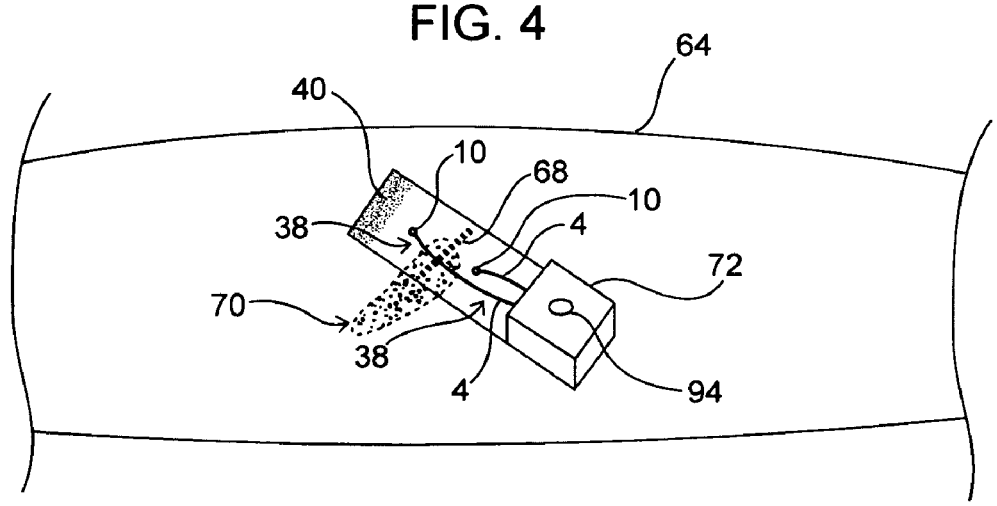

USER-RETAINABLE TEMPERATURE AND IMPEDANCE MONITORING METHODS AND DEVICES

FIELD OF THE INVENTION

The present invention relates to tissue monitoring, especially with apparatus suited for sustained or continued use by patients. Certain applications address concerns with wound healing including infection and subcutaneous fluid build-up, another addresses inflammation as in transplant rejection.

BACKGROUND OF THE INVENTION

Fluid accumulation and infection at the site of a wound can significantly hinder wound healing. Fluid accumulation can exert a detrimental mass effect upon adjacent tissue and compress vital anatomy or structures. Infection can result in tissue morbidity, rejection, fever, gangrene and even death.

Background discussion regarding fluid accumulation and tissue infection follows, in turn. That certain information is presented as background herein should not, however, be taken as indication that the present invention does not predate it.

With respect to fluid accumulation, if detected before significant damage occurs, it can often be treated by simple surgical intervention. For instance, lancing and/or drain insertion or implantation may provide adequate and continuing therapeutic relief.

Impedance measurement has been employed to measure volumetric changes of the body in certain applications. U.S. Pat. No. 4,805,621 to Heinze et al. discloses a system adapted to measure body tissue impedance, particularly to set the rate of a pacemaker by reference to volumetric measurement of a beating heart and thorax during respiration movement. Heinze neither discloses or suggests the use of local impedance differences to locate or monitor indicia negative of proper wound healing.

Regarding infection, it is well established that infection can be effectively treated by antibiotics. Also, antibiotics can be effectively administered prophylactically to avoid infection. However, this approach may not be desired for reasons ranging from drug interaction, to bacterial resistance to antibiotics. Regardless, it is desired and often necessary to repeatedly check, examine or monitor an area for infection—especially prior to administering antibiotics.

It is also known that infected tissue presents at a higher temperature relative to uninfected tissue. U.S. Pat. No. 6,135,968 to Brounstein teaches the use of temperature sensors affixed to an insulative support to fit over or be adhered to a probe (such as a finger) for accessing internal body locations via body orifices to effect temperature-based examinations. The preferred embodiments include two discrete temperature sensing regions allowing for comparative analysis of tissue temperature. As stated in the patent, an important function of the temperature sensor support in all embodiments of the invention is to insulate a temperature sensing patch from the fingertip of the user and thereby improve the accuracy of the sensed temperatures by isolating temperature sensed by the sensing patch from the influence of heat emanating from the user's fingertip. Closed cell polyurethane foam with a thickness of about 1 to 2 millimeters is disclosed as a suitably pliable and insulative material for the temperature sensor support.

By comparing the temperature of near-by healthy tissue with that of a suspect site, a diagnosis can be made as to the existence of abnormal subsurface tissue activity such as the growth of malignant tumors, benign neoplasms, infections and/or inflammations. The devices involved and examination techniques disclosed are, however, by no means suited for long-term infection monitoring.

One recently disclosed device is, however, suited for sustained monitoring of wounds for infection. In a Nov. 5, 2001 issue of Medical Industry Today, a story was run reporting that the University of Rochester had taken steps toward creating a bandage that will change color depending on what kind of bacteria may be present in a wound. The bandage was disclosed as capable of giving an instant diagnosis as to whether the wound may require special care or what kind of antibiotics would work best in treating it. A silicon-based sensor is employed to differentiate between Gram-positive and negative bacteria. Indication of further application include similar sensors to identify several other types of bacteria, with particular focus on research directed toward antibiotic resistant strains. As embodied in a "smart bandage," the sensor is said to function in connection with a type of molecule called "lipid A" on the surface of Gram-negative bacteria. When a complementary molecule linked to or part of the sensor binds to lipid A, the sensor changes color.

The article indicates that color change of the sensor is subtle and could be missed by a human eye. Accordingly, reading by an ancillary device is discussed. One embodiment envisioned for the bandage includes an array of dozens of different bacterial sensors that will change color dramatically enough so a glance inspection will alert the user to a serious infection.

Potential non-medical applications are also disclosed in which, for example, a drinking vessel or wrapping around a package of ground beef would change color to caution a user in the event of the presence of certain bacteria. Further potential applications envisioned include providing early warning against biowarfare.

The breakthrough described in association with the development of the bandage was detecting and identifying a single, distinct species of bacteria. Further development possibilities were linked in the article to finding molecules that detect other bacteria. In any case, the silicon sensors only have bacteria-specific wound monitoring capability. Furthermore, even if the prophesized sensor arrays come into being, they will only detect such forms of bacteria corresponding specifically to the array elements. Accordingly the smart bandage approach taught in the article lacks general applicability. To remedy this, the article merely suggests searching for molecules capable of detecting other bacteria to add functionality in a piecemeal fashion.

SUMMARY OF THE INVENTION

The present invention is geared toward broad-based detection of wound and/or implant-related complications. Sensors registering local temperature differences give indication of infection. Temperature sensing aspects of the invention also find use in monitoring other conditions such the progression to completeness of normal wound healing, the state of anesthetized tissue, local immune responses to vaccinations, the flow of blood to muscle flaps or other tissues and the margins of viability of tissues affected by burns or frostbite. Impedance sensing provides indication of fluid build up or the volumetric status at a site. Such methodology may be used in monitoring for post-surgical hematomas, and proper functioning of devices such as shunts, grafts and drains.

In serving each such use, the present invention integrates sensors formats that are amenable to prolonged retention by a patient. Holding the sensors in close anatomic association with a subject or patient for an extended period through the use of an easily-retainable support allows for constant or periodic monitoring by a patient, physician or other care provider.

User retainable formats include support structures suited for external as well as internal use. In addition to those described herein, further uses, advantages and features distinguishing the present invention may also be apparent to those with skill. The various apparatus as well as associated methodology described herein form aspects of the present invention.

BRIEF DESCRIPTION OF THE DRAWINGS

Each of the following figures provides examples diagrammatically illustrating aspects of the present invention. Like elements in the various figures are indicated by identical numbering. For the sake of clarity, some such numbering has been omitted.

FIGS. 2A–2J show views of various support member types as may be used in the present invention.

FIGS. 3–6 show monitors according to the present invention in use.

DETAILED DESCRIPTION

Figure 1A:
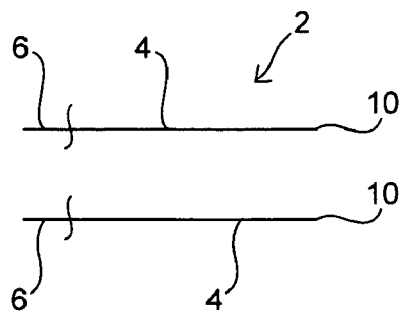
FIGS. 1A–1D show views of various sensor types as may be used in the present invention.

In describing the invention in greater detail than done above, the subject monitoring system and underlying technology are addressed first, followed by examples of apparatus produced according to the present invention and associated methodology. Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims made herein. Furthermore, where a range of values is provided, it is understood that every intervening value, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are described. All existing subject matter mentioned herein (e.g., writings, publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

Also, it is noted that as used herein and in the appended claims, the singular forms "a," "and," "said" and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely," "only" and the like in connection with the recitation of claim elements or the use of a "negative" claim limitation(s).

Variations of the present invention include temperature and/or impedance sensors provided in connection with a support element or member. The present invention takes forms that the a patient may wear (e.g., a bandage, strip, pad or patch, sleeve, bracelet, suction cup(s) or wrap) or retains internally (e.g., a shunt, catheter, drain or prosthesis), possibly by implantation. The form-factor employed determines whether monitoring is accomplished at or near the surface of the patient's skin or within the patient's body. Both the format of the apparatus and associated sensors may be configured to monitor for infection, near-by fluid accumulation or other indica. Continued use by a patient for (several) minutes, on the order of hours, days, weeks or longer is contemplated with the present invention. Use for an extended period of time is contemplated. Sometimes, a monitor according to the present invention will be worn or retained by a patient for up to 60 days or longer (as in the case of permanent or semi-perminent implants).

Before describing the various forms the invention may take, together with applications they are suited for, optional sensor types are first described. As shown in FIG. 1A, an impedance sensor 2 is provided using simple electrical leads 4. A proximal end 6 of each such sensor member is typically connected to a diagnostic instrument. Exemplary instruments, or components thereof, such as described in U.S. Pat. No. 4,805,621 to Heinze et al.; U.S. Pat. No. 4,837,501 or U.S. Pat. No. 5,068,618, each to Fry et al. or other circuitry able to measure body tissue impedance may be used in connection with these sensor members.

In operation, AC current or voltage is applied through the leads via a predefined spectrum of frequencies or selected single frequencies as needed. For impedance sensor variations of the invention, there will always be at least two electrodes, since one needs a source and sink for current (in this case, alternating current).

Changes of the impedance of tissue to current flow varies as a function of the state of the tissue. The attenuation of current flow through tissues is a function of the biological properties of the same as well as the frequency of the current. Normal and pathological states demonstrate different impedance profiles. The presence of or changes in these profile(s) correlate with different physiological states. Additionally, the penetration of AC currents is frequency dependent. So, for a given case, such as searching for hematomas post-surgically, an appropriate selection of frequencies should yield the ability to "look" deeper or shallower in the tissue.

Whether provided as described in the above-reference patent(s) or otherwise, a current or voltage generating means is coupled to the sensor members for use. In addition, voltage or current detecting means may be coupled thereto, or a specially adapted impedance sensing means may be utilized in connection with the impedance sensor members.

A distal end 10 of each lead or probe may directly contact body tissue or it may be in electrical contact with the body via pads, caps or another intermediate interface member. The same is true for the other sensors disclosed herein. Some part may be placed in direct contact with a user or an intermediate layer of material or member may be present. Especially in connection with temperature sensors, any such structure preferably enjoys a high thermal conductivity or is at least so thin that it interferes little with patient temperature sensor readings.

Figure 1B:
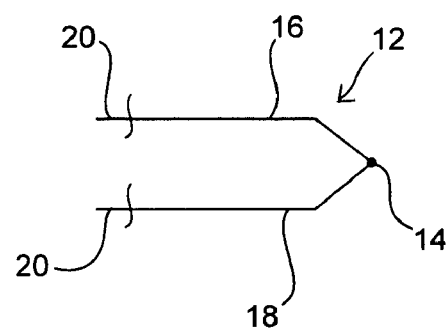

FIG. 1B shows a first type of temperature sensor that may be used. A thermocouple 12 is shown. A thermocouple is provided by a junction 14 between two dissimilar metallic conductor leads 16 and 18. A proximal end 20 of each lead connects the thermocouple to appropriate hardware for use.

The junction between the two metals generates a voltage which is a function of its temperature and the type of metals employed. The temperature at the junction can be determined by measuring the voltage via leads connected to appropriate hardware in reference to tabular data or by using various algorithms describing a given thermocouple's performance. While most thermocouple types are appropriate for use in the present invention, T, J or K-type devices may be preferred because of their common nature and/or relative stability in temperature measurement. Of course, the construction and operation of thermocouples is well-known in the art.

Figure 1C:
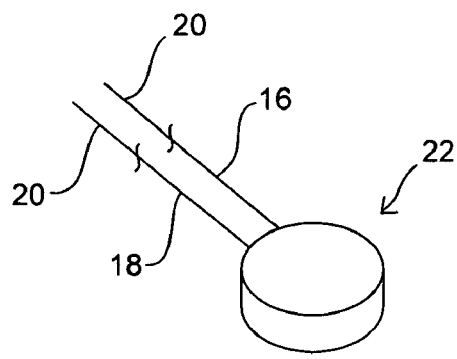

Another sort of temperature sensor that may be employed in the present invention is commonly known as a thermistor. A thermistor is a semiconductor device that senses and detects temperature by measuring electrical resistance. The silicon material of which a thermistor is typically made has a resistance that varies with temperature due to the semiconductor material's high temperature coefficient of resistance. FIG. 1C shows a disk-shaped thermistor 22 that may be used in the present invention. Ends 20 of leads 16 and 18 connect the thermistor to appropriate hardware for use. The fabrication and operation of thermistors is also well known in the art.

Still other types and/or formats of temperature sensor members may be employed. For instance, junction-based thermal sensors (e.g., diode or transistor temperature sensors), thermopile, fiber optic detectors, acoustic temperature sensors, quarts and other resonant temperature sensors, thermo-mechanical temperature sensors or thin film resistive elements may also be used. Detailed discussion of many of these devices is presented in the "Micromachined Transducers Sourcebook," by Gregory T. A. Kovacs, published by McGraw-Hill 1998. Other information regarding the sensors is well known in the art.

With respect to any of the temperature sensors (those named and others known in the art), any of their common configurations may be employed even though only certain examples are illustrated in the figures. For example, though FIG. 1C shows a disk-shaped thermistor 22, other suitable common thermistor configurations include ceramic beads, chips, rods, washers, glass encapsulated beads, etc.

Based on the type(s) of temperature sensor selected, certain collateral hardware may be required. While colorimetric temperature sensors are self-contained and can be read without the aid of equipment, the same may not true for all other types. One with skill in the art will easily appreciate what sort of equipment need be connected or coupled to the temperature sensors for taking measurements or detecting a temperature difference between at least two sensors. Further, the manner in which electronic memory may be coupled to store or record data taken to assist in diagnosis will be readily apparent.

Regarding such hardware that may be provided in connection with temperature sensors (or impedance sensors as discussed above), it may be provided in stand-alone system or monitor that the sensors (or a buss which the sensors are connected to) mate with. Alternately, some or all of the hardware may be packaged with the sensors and the support structure selected. Another possibility is that a portion of the hardware that is used for data acquisition or interpretation is packaged with the sensors and the remainder resides at a standalone location. Either a physical connection or remote/telemetry type connection may be employed in this regard. which the present invention is connected to directly or via some form of remote connection.

RF signals sent and received by first and second telemetry units, respectively may be employed. An exemplary system applicable to such use is disclosed in U.S. Pat. No. 6,083,174 to Brehmeier-Flick. Other telemetry units and applications thereof well known in the art are also applicable to the present invention.

Regardless, transmission of data to other diagnostic and/or data storage device(s) may be carried out in burst or continuous fashion as described variously. Telemetry for use in the home is contemplated. In the case of a hospitalized patient, telemetry of data to a central Intensive Care Unit (ICU) station provides another example of use.

In some variations of the invention, it will be preferred to include a storage device attached to sensors directly to store data indefinitely. Such an approach makes for a self-contained device that can be periodically interfaced with a diagnostic instrument.

Regardless of the configuration, data storage may advantageously be used in connection with the sensor chosen in a variety of ways. For instance development or resolution of an impedance profile, stored over time, between at least a first and second sensor members can signify a biological state of interest. Examples of such states include the development or resolution of absence of fluid or air collection, and the progress of tissue swelling (immunologic proliferation), together with related physiological changes. Further, storage of impedance data can facilitate comparison of the measurements taken against a look-up table or database to assist in diagnosis.

Still, an impedance profile generated between at least a first and a second sensor member locations, at a particular instant, may signify a biological state of interest. Examples of such states include: 1) the presence or absence of fluid as in a hematoma, inflammatory mass, abscess or infection; 2) the presence or absence of air as in a pneumothorax; or 3) the presence of a foreign body in tissue.

A number of useful observations can be made with respect to stored temperature data as well. Both the development and/or resolution of infection can be monitored (even deep to the skin) through observation of stored sensor data. Additionally, the normal (uninfected) healing of a wound may be observed. Just as infection results in increased temperature of tissue, so does the healing process, though generally to a lesser degree.

As normal wound healing progresses, wound temperature decreases to baseline after about 72 hours. Accordingly, by observing a return to normal temperature, an indication of completed wound healing is available. Conversely, an observation of continued elevation in temperature after 72 hours indicates the presence of an infection. Where wound infection occurs, the temperature remains elevated or climbs, usually over that of normal (i.e., uninfected) tissues.

Other indications that may be observed through detection of development or resolution of a temperature difference, over time, between at least a first and second include monitoring a diagnostic injection site for signs of immunological proliferation or reactivity such as a TB tine test and monitoring the state of a chronically inflamed tissue, including rheumatoid inflation or other chronic autoimmune disease. Where temperature is measured over a period of time, indication of a biological state may be derived from temperature measurement parameters such as temperature difference, or average temperature over a period of time. As with monitors using impedance to observe biological states, temperature data obtained over a period of time may be compared to a look-up table or database. The use of such "categorized" data may be of great assistance in drawing conclusions based on the data obtained.

Still further temperature-based methods according to the present invention involve determining pathological state of in view of the presence or absence of a temperature difference between tissue regions, at a particular instant. Examples of such indications that may be detected in this manner include:1) vascular compromise to a tissue after trauma or in occlusive vascular disease; 2) vascular compromise to a surgically modified tissue such as an AV fistula for dialysis, or a reconstructive muscular flap procedure or other procedure requiring vascular anastomosis, or organ or tissue transplant; 3) detecting the boundary of viable tissue after an insult such as after a severe burn or frostbite, or after infection with tissue destroying organisms such as clostridium perfringes; 4) in intraoperative monitoring of tissue where direct application of energy may impart excessive damaging heat such as during phacoemulsification of the lens of the eye, or tympanoplasty of inner ear, or during procedures involving eletrocautery or electrocoagulation, or during procedures involving the administration of heated agents such as high temperature chemotherapy, or thermal ablation of tumors; 5) likewise, in intraoperative monitoring of tissue where direct cooling may impart excessive damage to surrounding tissue such as cryoablation of tumor; 6) in monitoring of tissue during procedures for diagnosis or therapy such as intraoperative cardiac perfusion monitoring or thermal dilution methods 7) in monitoring the state of local anesthesia due to the administration of anesthetic agents, or in the condition of sympathetic nerve block, or autonomic dysfunction, and 8) immunological rejection of organ transplants. For such indications, a temperature-based diagnosis may be achieved by observation of a temperature rises/fall past a predefined limit once or observation of a temperature rises/fall past a predefined limit for a predetermined period of time. In addition, a diagnosis may be made from observation of raised or lowered temperature at one sensor location relative to a reference temperature sensor location.

It is noted that in instances where temperature and impedance are monitored over time (especially as facilitated by storage and processing of results) to make a diagnosis, that there may be no need to seek a remotely-located reference against which to compare wound temperature or impedance measurements. However, especially with temperature-based systems according to the present invention where instantaneous results are desired, a reference measurement as well as a site-specific measurement is taken.

Figure 1D:
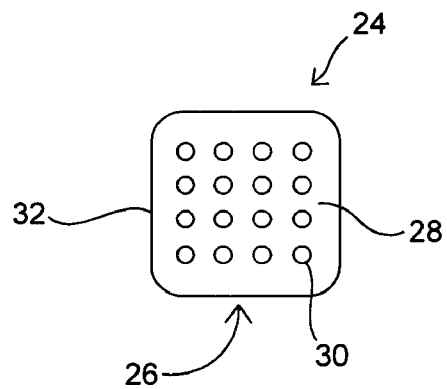

One type of sensor that lends itself to at-a-glance data acquisition is a calorimetric temperature sensor 24. An example of such a temperature sensor is shown in FIG. 1D. Such colorimetric temperature sensors are known.

The temperature sensor pictured includes a grid of temperature-sensitive chemical indicators 30 deposited on a heat transmissive backing 32. The breakdown of indicators and an associated legend (not shown) or printing on the indicator panel can be used to allow a user to properly read the temperature based on the state of the indicator dots.

The indicators may be comprised of a layer of encapsulated cholesteric liquid crystals, ortho-bromonitrobenzine, ortho-chloronitrobenzine or materials such as those described in U.S. Pat. No. 4,232,552 to Hof et al., although a variety of other materials may also be used. Preferably, the composition selected is such that upward and downward fluctuations in temperature are registered in an instantaneous or near-instantaneous manner in order to facilitate repeatedly checking the temperature of a site.

FIGS. 2A–2G show the various types of support members mentioned above, with optional sensor member placement locations indicated by arrows. In each of them, at least two sensor locations are shown.

With impedance sensors, where two sensor locations are provided, each location corresponds to the end of an electrical lead 4. In such case, only one set of data (at a particular frequency) is generated. With temperature sensors, where two sensor locations are provided, separate or distinct temperature readings are provided at each location to give comparative temperature readings.

Of course, as illustrated in the figures, more that two temperature sensors may be provided. Likewise, several impedance sensors may be employed, instead of just one having a pair of spaced-apart probes.

Hardware configured to include at least two sensor locations is specifically adapted to the methodology contemplated by the present invention and is therefore most preferred. Still, the methodology described in connection with FIGS. 3–6 below may be carried out otherwise. For instance, it may be carried out with discrete sensors that are not carried by a single support structure.

Figure 2A:
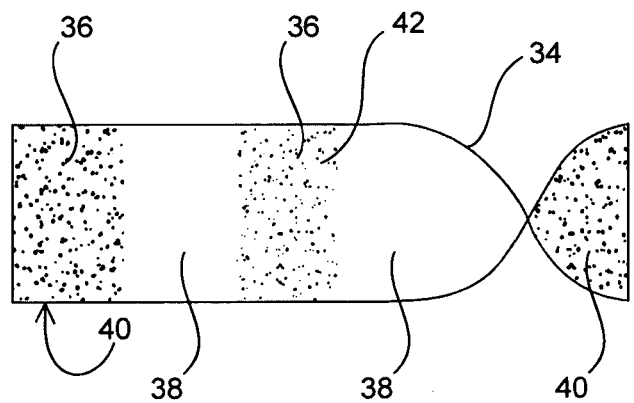

As for what is preferred, however, FIG. 2A shows a bandage 34 with spaced-apart temperature sensor locations 36 and/or impedance sensor locations 38. The bandage preferably includes adhesive sections 40 and a pad or gauze area 42.

For use in monitoring temperature, one sensor region 36 is preferably centered on the bandage in order to register wound temperature, whereas an adjacent sensor location 36 offers a baseline temperature. The points where temperature readings are taken should be separated by such a distance that a baseline temperature reading from one sensor is unaffected or not substantially affected by the temperature of whatever tissue that the other sensor is positioned to monitor. Stated another way a first sensor is set in proximity to undisturbed normal biological tissue and at least a second sensor is mounted proximally to the first sensor at the site of disturbed biological tissue, which was subject to a traumatic incision or other action producing the wound. Sensor separations of at least 1 cm may be approximate in certain cases.

Yet, base-line temperature sensor(s) locations(s) should be set so that temperature readings produced are properly comparable to the site to be monitored. For example, when an external wound is to be monitored according to the present invention, an adjacent patch of skin will produce an appropriate baseline temperature for comparison—whereas an internally taken temperature may not since it will not be exposed to the same environmental conditions as the site of interest that may cause temperature fluctuations.

The distance between impedance sensor members will also vary from one application to another. It may depend on the form-factor of the device(s) used or based on other factors. That is to say, sensor member spacing will vary from case-to-case. Appropriate spacing may be determined by those with skill in the art in view of the particular issue faced.

For use in monitoring for sub-surface fluid accumulation, preferred sensor element locations may differ from those employed for temperature sensors. To use an impedance sensor most effectively in monitoring a wound, the portion of its probes or electrodes in electrical contact with a patient should straddle at least a portion of the wound. Alternately, side-to-side, top-to-side, or top-to-bottom placement of sensor members relative to a wound, limb or other structure to be monitored may prove effective, depending on the circumstances.

It is contemplated that the bandage or any other support member as may be used in the present invention can be configured to monitor both temperature and impedance. In which case, staggered or spaced-apart sensor locations may be employed. Alternately, it may sometimes be feasible to use a shared set of sensor locations.

Figure 2B:
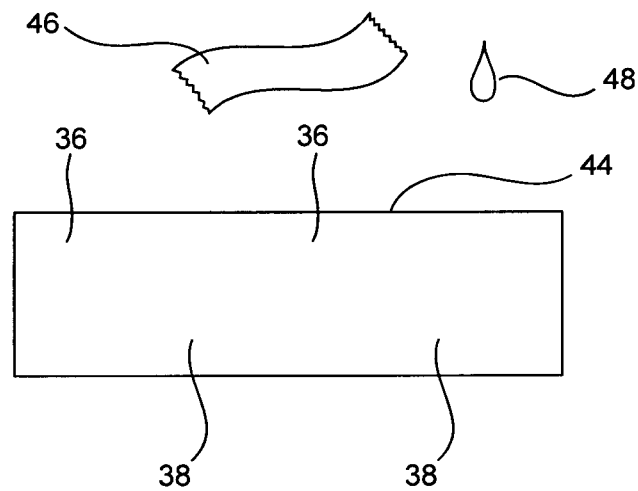

FIG. 2B shows a simple strip 44 serving as a support member. The strip may be a polymeric member or made of another material. It includes various sensor placement locations 36 and 38. Such a support device is optionally retained by a patient through the use of tape 46 or adhesive 48 applied to a the skin.

Figure 2C:
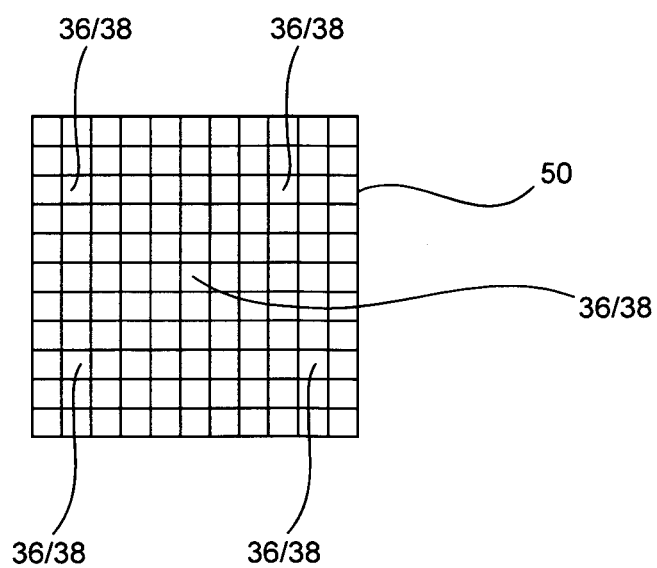

FIG. 2C shows a patch or plate 50 as may be used as a support member. It may comprise a cotton or synthetic or fabric, alternately it may be made of foam, a flexible polymer or a corrosion resistant metal such as titanium. Generally, it is preferred to use support members that are not substantially thermally conductive. It may cover a larger area and include a grid or matrix of sensor locations 36/38. It may be affixed to a patient by tape, another fixative or otherwise. Further, it may be implanted.

Figure 2D:
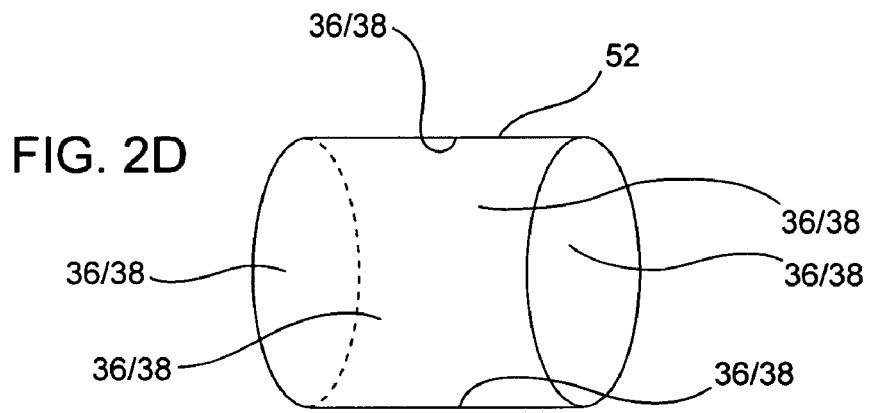

Instead of affixing or adhering a sensor support structure to a patient, it may be retained by a patient or subject otherwise. FIG. 2D shows a sensor support sleeve or cuff 52. It too includes a plurality of sensor locations 36/38, placed as may be suitable for detecting the temperature at one or more monitoring sites and one or more reference locations or impedance at one or more sites. Such sensing may be at opposite sides of the sleeve. A sleeve can be expanded to fit over a digit or appendage and remain situated by elastic material incorporated into a portion of the sleeve or the entire device.

Figure 2E:
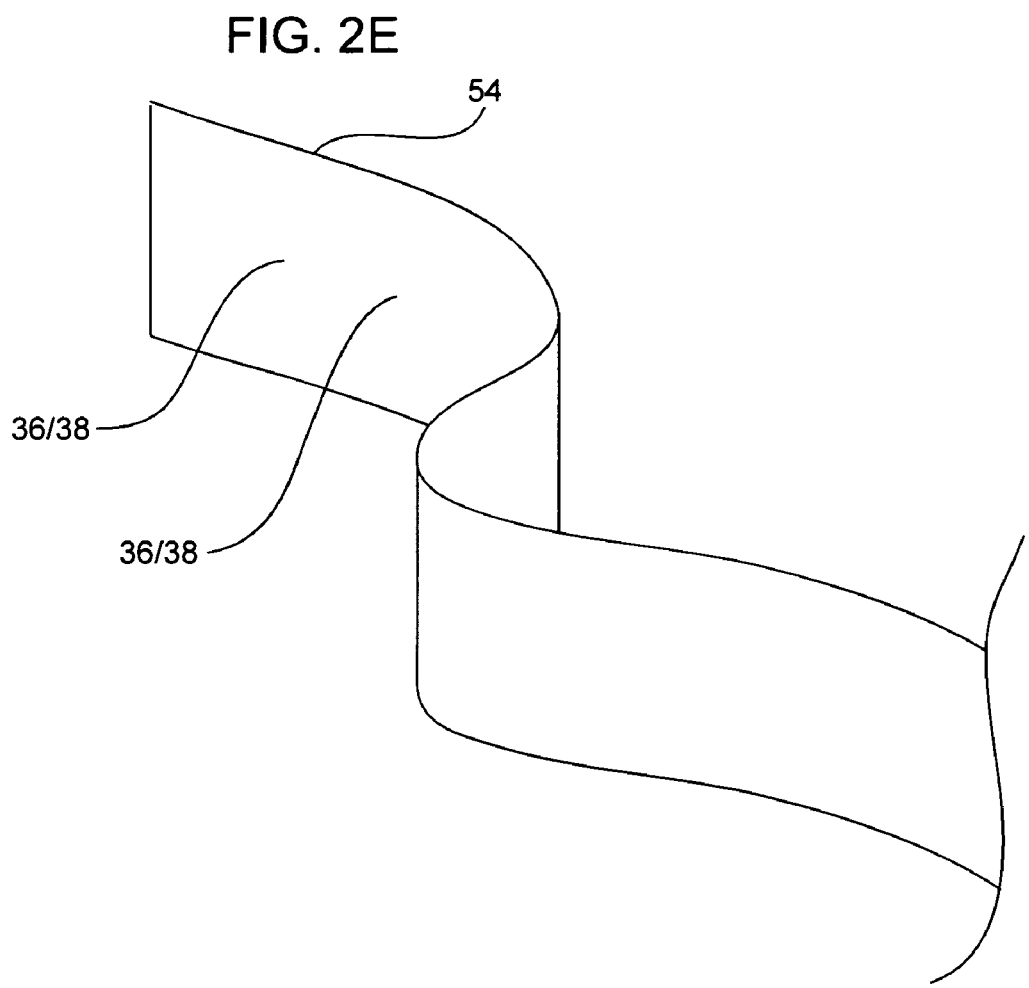

Yet another approach for a sensor support to be worn by a user is presented by the use of a wrap 54 as shown in FIG. 2E. Sensors locations 36/38 are shown adjacent one end. However any sort of convenient placement may be selected. Elastic wraps or wraps made of non-elastic material may be employed.

Still further, a bracelet 96 may be utilized as a support member. As shown in FIG. 2H, the bracelet may include an adjustable interface 98. Various sensor location options are possible as with the other devices described herein.

Further possible support members include, suction cup member(s) 100/100' as shown in FIG. 2I. A singe suction cup may be employed, or a plurality of associated members may be used. Any convenient means may be employed to associate at a desired distance or spacing such as a tie-bar 102 as shown. As to sensor location, in a single-cup type system, a plurality of sensor members will be associated or embedded in the structure. Where a multiple-cup system is provided, each may include as few as a single sensor location 36/38.

Additional examples of possible sensor support structures also include prosthetic members 104. FIG. 2J illustrates prosthetic knee components 106. As in the preceding examples, sensor locations 36/38 may be located variously.

Figure 2F:
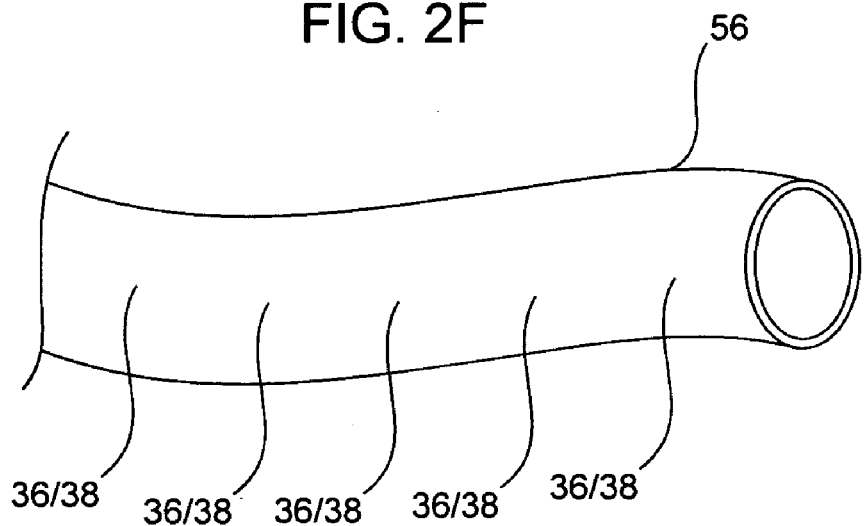
Figure 5:
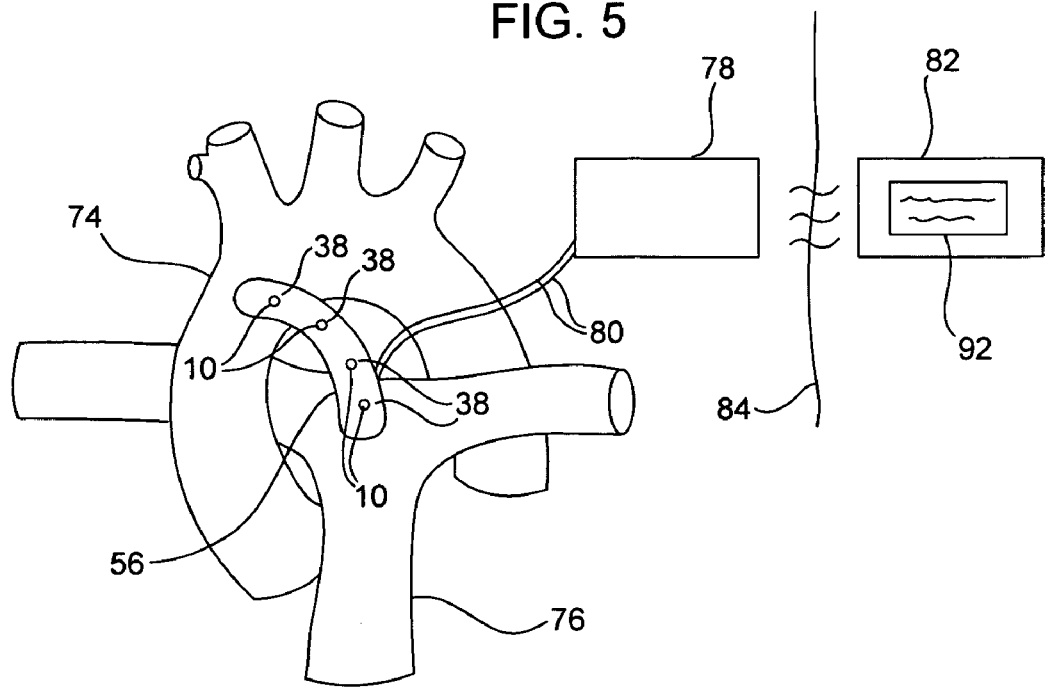

FIG. 2F shows an example of a sensor support in the form of a shunt or graft tube 56. Typically, a shunt is little more than a conduit attached between two natural body fluid pathways to redirect flow or provide access to a given flow path. An exemplary shunt application is hemodialysis, usually between the radial artery and cephalic vein. Shunts find use in other applications as well, such as in communicating blood from a patient's aorta to pulmonary artery as illustrated in FIG. 5. A plurality of sensor locations are shown along the body of shunt 56.

Figure 2G:
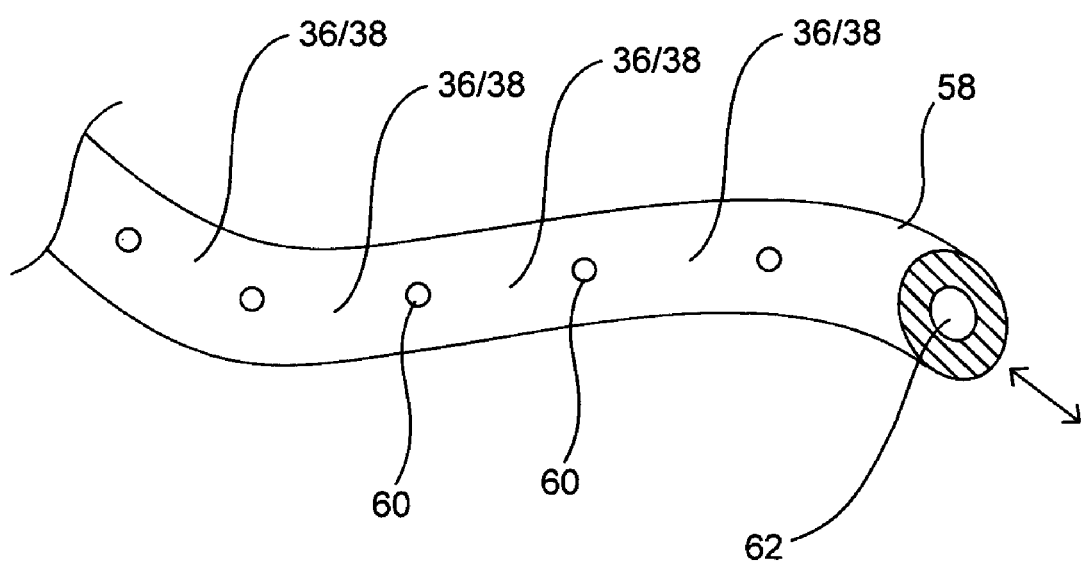

FIG. 2G shows a drain or catheter 58. As with shunts, such devices may take various forms. Drains are typically used to evacuate or establish an exit route for fluids or purulent material from any cavity or wound. Infusion catheters are often used to deliver drugs for thereby. An end section of a perforated drain or catheter is shown. Orifices 60 conduct fluid to or from a central lumen 62. Of course, other drain or catheter configurations may be used in the invention. Multiple-lumen designs are common. To infuse drugs or fluid irrigants, device 58 may be connected to a pump. To assist in evacuation of fluid, the device may be connected to suction. Either action is indicated by the double-arrow in FIG. 2G.

At a point upstream from the section shown in hatching, the drain or catheter exits the body, through the wound itself that is being monitored or through remote stab incision. Temperature and or impedance sensors are preferably provided at locations 36/38 in the region of the implanted portion of device 58 since sensors in this region will be capable of producing useful data.

Indeed, sensor members according to the present invention may be incorporated in any sort of implantable or semi-implantable device such as those described above, variations of certain devices (e.g., the catheter may be configured as a urinary and cardiac catheter), or other implant prosthesis devices. The manner in which implantable or semi-implantable support structures according to the present invention are retained by a patient may vary. A shunt may be secured using common techniques such as suturing. The length of a drain is usually held in place largely by virtue of its location, while its external portion is secured by suture(s) or tape to a patient's skin.

Both the drain or catheter and shunt advantageously include temperature and impedance sensors. Combined ability to sense for infection and fluid volume has particular applicability with these variations of the present invention. High incidents of infection are often associated with implants, especially those with partial external exposure.

Actually, fluid-sensing capability of the present invention, when employed in shunts, grafts, infusion catheters and drains (and the like) offer the ability to monitor the efficacy/function of the devices. Accumulation of fluid (or the lack thereof) may indicate clogging, misplacement or another malfunction.

With implantable or semi-implantable variations of the invention, the sensors types included in FIGS. 1A–1C are preferred. Each of these sensor types is readily monitored remotely by electronic means while the device is in situ.

It is contemplated that other types of electronic sensors may be incorporated in such devices as well (e.g., sensors able to detect biochemicals associated with healing. Further, sensors as described above that are able to detect particular bacteria may be employed.

Whatever the type of sensor employed, it is contemplated that the manner in which sensors are carried by any of the various sensor support structures disclosed may be varied. Where laminate constructions are preferred, sensors may be located between layers. Of course, sensors may be surface-mounted on the respective support structures. Other times, they will be set at their respective locations within the body of the support structure.

In instances where a layer of material is provided between a given sensor member or a portion of a sensor, this layer should be conductive. With respect to thermal or temperature sensors, the material should at least be thermally conductive, rather than insulative. With respect to impedance type sensors, the material should at least be electrically conductive, such as conductive electrolyte gels, polymers or pastes or fabrics impregnated with such conductive or semiconductive materials.

Particular hardware configurations for practicing methods according to the present invention are shown in FIGS. 3–6. In FIG. 3, a patient's forearm 64 is shown wearing an external monitor 66 according to the present invention over a wound 68. In this very basic variation of the invention, a bandage 34 is affixed to the skin of a patient by adhesive regions 40. First and second temperature locations 36 include (or are filled by) calorimetric temperature sensors 24.

The temperature of the wound and the temperature of an adjacent location is registered via the sensor patches 24 while monitor 66 is in place. Accurate temperature readings are obtained by thermal conductance through the sensor backing or any intermediate support layers. By checking the status of the sensors, the status of the wound may be determined.

When a sensor more amendable to electronic monitoring is used (such as those in FIGS. 1A–1C), checking the status of a wound or another site of interest may be done automatically, including signaling values beyond a desired range. Such an approach may be easily implemented with hardware and software as readily apparent to one with skill in the art.

FIG. 4 shows a bandage including spaced apart impedance sensor members/leads/terminals 4 in connection with a patient's arm 64. Ends 10 of each impedance sensor member are set at locations 38 straddling wound 68.

With impedance sensing (preferably on either side of the wound), by using various data processing techniques, the status, including location of a region of fluid accumulation 70 beneath the skin can be detected. Such processing may be accomplished by hardware (and any associated software or logic) which the sensor leads are connected to. Alternately, certain hardware may be provided by on-board hardware 72 carried by the sensor support member. The same is true in situations where temperature sensors are employed or where both temperature sensors and impedance sensors are employed.

Any such on-board hardware may include power supplies, memory, microchip processors and/or telemetry units. Memory may be used to record data for later analysis and/or store programming to run included hardware. A telemetry section of the on-board hardware may be included to avoid the need to make a physical connection with external hardware to obtain or retrieve data FIG. 5 shows another monitor employing self-contained hardware. Here a shunt 56 is shown attached between a patient's aorta 74 and pulmonary vein 76.

Impedance sensors probes 10 are provided at spaced apart locations 38 along the device to monitor the surrounding area to give an indication whether the device it remains open and situated to properly pass blood between the anatomical structures.

A hardware support packet 78, including circuitry for measuring impedance, a telemetry unit and such other features as desirable is provided in the variation of the invention shown in FIG. 5. It is provided separate from the shunt, but connected via electrical leads 80. The location of the hardware may be remote from the sensors, yet fully implanted to minimize issues associated with infection. By implanting it near the surface of the skin, a counterpart unit 82 may be readily employed with inductive interface to recharge packet 78. Implanting such a packet near the skin 84 of a patient or subject's body also reduces the power requirements of telemetry units used to transmit data acquired by the monitor to external hardware.

Figure 6:
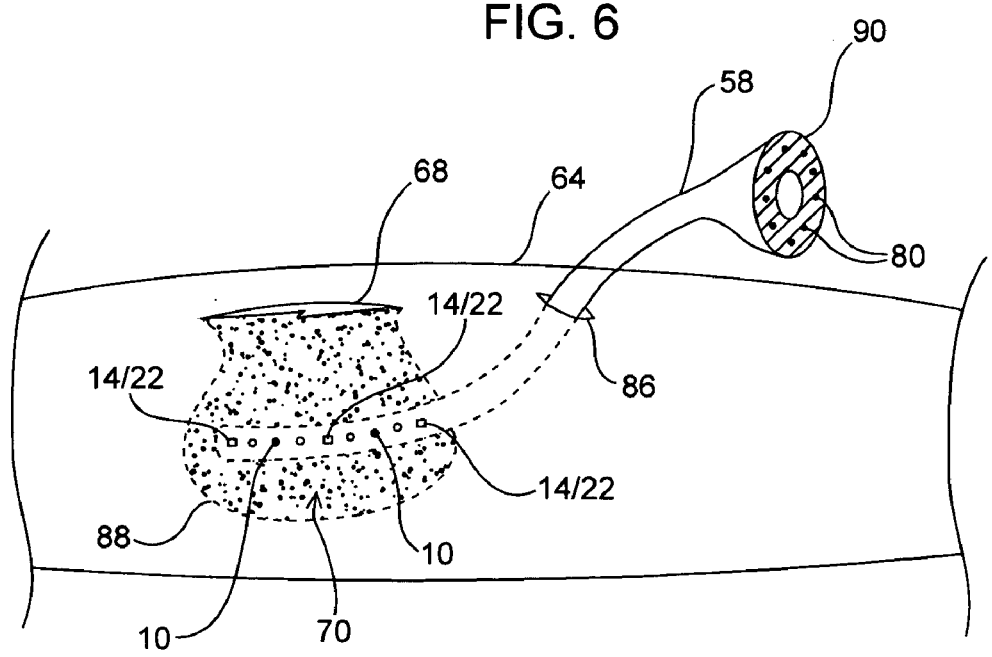

FIG. 6 illustrates the use of another type of monitor and methodology according to the present invention. Again a patient's forearm 64 is shown in connection with a wound 68. A drain or catheter 58 is inserted through a stab 86 in the arm to release or evacuate fluid 70 from a cavity 88 below the wound entry. Alternately, access to the cavity 88 may be had through the wound incision.

The drain includes both temperature and impedance sensors located at intervals along the body of the device. Thermisors or thermocouples are equally preferred for use as the temperature sensors. Lead wires 80 from the sensors are preferably included in the device body 90 for connection to support hardware. This preferred relation is shown magnified at a section taken in the device.

Such lead wires interface with hardware that preferably regularly monitors the temperature status and/or impedance provided by the sensors. Certain programming to sound an alert or take remedial action such as to increase or adjust suction from a drain, prompt adjustment of the shunt or increase the rate of drug delivery from a catheter may be employed in response to data taken from such monitors and others according to the present invention.

In many instances, the programmed action for hardware in association with any of the monitors will be to make and display a diagnosis based on sensor results. The type or nature of any such diagnosis and/or display may be of the sort referenced herein, in any of the documents incorporated by reference or otherwise. A monitor display 92 as shown in FIG. 5 (but optionally incorporated in other hardware) is preferably provided so that complex messages or instructions can be communicated to a user or a physician. Alternately, a simple indicator 94 such as a light emitting diode as included in the hardware in FIG. 4 may be provided to light up or change color to indicate a condition relating to sensor results. Hardware to sound an audio alarm or provide audio instructions to a user of a monitor according to the present invention may also be provided.

In addition to (or instead of) providing alarms or user instructions, the monitors may be programmed and include such hardware or be interfaced with such equipment as to allow it to direct remedial action. That is to say, monitors according to the present invention may activate secondary devices to perform therapy such as deliver therapeutic medications after triggered by an impedance change or profile or a temperature change or profile.

It is contemplated that various features of each of the embodiments shown may be used with another. Furthermore, methodology most preferably carried out with the variations of the invention disclosed may be carried out otherwise. For example it is contemplated that temperature sensors used to make comparative temperature readings need not be carried by or be integral with a single support member. Especially for variations of the invention taking internal temperature readings, obtaining a reference temperature at an area far remote from an area to be monitored or studied may even be preferred. Still, including multiple temperature sensors along the length or surface of an internal monitor according to the present invention can provide advantages in terms of pinpointing infection or inflammation such as in transplant rejection or autoimmune diseases such a rheumatoid arthritis in relation to any portion of the device.

Further, as noted above, methods according to the present invention using repeated temperature sensing are not limited to monitoring wounds but also include monitoring the state of locally anesthetized tissue, blood flow to muscle flaps or skin, tissue affected by burns, frostbite or immunologic rejection of organ transplants. The status of each indication is linked to blood flow and, hence, the temperature which the tissue will present at. With respect to producing systems for monitoring any of the latter indications that may recede or advance, a number of individual temperature sensors may be aligned in a series, grid or matrix as shown in connection with the sensor support in FIG. 2C to allow tracking of the situation.

In addition, the present invention is applicable to situations where the patient to be monitored is a viable fetus. For example, a monitor may be affixed to or retained by a subject of fetal surgery. Also, monitoring (especially impedance-based monitoring) may be used to guard against hydronephrosis, involving fluid accumulation and pressure build-up on the kidney or interuterine conditions such as oligohydramnios or polyhydramnios.

Additional potential applications of aspects of the present invention—and background regarding those mentioned above—are described in connection with the following writings: Stein, L. E., et al., *A comparison of steady state and transient thermography techniques using a healing tendon model* Veterinary Surgery, 1988. 17(2): p. 90–6.; Horzic, M., K. Maric, and D. Bunoza, *The temperature dynamics during the healing processing of a surgical wound.* Biomed Tech (Berl), 1995. 40(4): p. 106–9.; Viitanen, S. M. and J. Viljanto, *Wound healing. A thermographic study.* Annales Chirurgiae et Gynaecologiae Fenniae, 1972. 61(2): p. 101–6.; Kliot, D. A. and S. J. Bimbaum, *Thermographic studies of wound healing.* American Journal of Obstetrics & Gynecology, 1965. 93(4): p. 515–21.; Horzic, M., D. Bunoza, and K. Maric, *Three-dimensional observation of wound temperature in primary healing.* Ostomy Wound Manage, 1996. 42(8): p. 38–40, 42–4, 46–7.; Horzic, M., D. Bunoza, and K. Maric, *Contact Thermography in a study of primary healing of surgical wounds.* Ostomy Wound Management, 1996. 42(1): p. 36–8.; Waterman, N. G., L. Goldberg, and T. Appel, *Tissue temperatures in localized pyogenic infections.* American Journal of Surgery, 1969. 118(1): p. 31–5.; Golbranson, F. L., E. G. Yu, and R. H. Gelberman, *The use of skin temperature determinations in lower extremity amputation level selection.* Foot & Ankle, 1982. 3(3): p. 170–2.; Stoner, H. B., L. Taylor, and R. W. Marcuson, *The value of skin temperature measurements in forecasting the healing of a below-knee amputation for end-stage ischaemia of the leg in peripheral vascular disease.* European Journal of Vascular Surgery, 1989. 3(4): p. 355–61.; Sandier, D. A. and J. F. Martin, *Liquid crystal thermography as a screening test for deep-vein thrombosis.* Lancet, 1985. 1(8430): p. 665–7.; Gaiziunas, A. G. and M. H. Hast, *Temperature gradients and prediction of flap viability.* Journal of Otolaryngology, 1976. 5(5): p. 399–402.; Holmstrom, H., *Temperature changes of wound fluid inbipedicle tube flaps. An experimental study.* Scandinavian Journal of Plastic & Reconstructive Surgery, 1973. 7(2): p. 102–4.; Hackett, M. E., *The use of thermography in the assessment of depth of burn and blood supply of flaps, with preliminary reports on its use in Dupuytren's contracture and treatment of varicose ulcers.* Br J. Plast Surg, 1974. 27(4): p. 311–7.; Frank, S. M., et al., *Temperature monitoring practices during regional anesthesia* [see comments]. Anesthesia & Analgesia, 1999. 88(2): p. 373–7.; Park, E. S., et al., *Comparison of sympathetic skin response and digital infrared thermographic imaging in peripheral neuropathy.* Yonsei Medical Journal, 1994. 35(4): p. 429–37.; Palmer, J. B., et al., *A cellist with arm pain: thermal asymmetry in scalenus anticus syndrome.* Archives of Physical Medicine & Rehabilitation, 1991. 72(3): p. 237–42.; Pogrel, M. A., C. McNeill, and J. M. Kim, *The assessment of trapezius muscle symptoms of patients with temporomandibular disorders by the use of liquid crystal thermography.* Oral Surgery, Oral Medicine, Oral Pathology, Oral Radiology, & Endodontics, 1996. 82(2): p. 145–51.; Robicsek, F., et al., *The application of thermography in the study of coronary blood flow.* Collected Works on Cardiopulmonary Disease, 1979. 22: p. 49–56.; Robicsek, F., et al., *The value of thermography in the early diagnosis of postoperative sternal wound infections.* Thoracic & Cardiovascular Surgeon, 1984. 32(4): p. 260–5.; Saxena, A. K., et al., *Thermography of Clostridium perfringens infection in childhood.* Pediatric Surgery International, 1999. 15(1): p. 75–6.; Cole, R. P., et al., *Thermographic assessment of burns using a nonpermeable membrane as wound covering.* Burns, 1991. 17(2): p. 117–22.; Ferguson, J. C. and C. J. Martin, *A study of skin temperatures, sweat rate and heat loss for burned patients.* Clinical Physics & Physiological Measurement, 1991. 12(4): p. 367–75.; Boylan, A., C. J. Martin, and G. G. Gardner, *Infrared emissivity of burn wounds.* Clinical Physics & Physiological Measurement, 1992. 13(2): p. 125–7.; Wyllie, F. J. and A. B. Sutherland, *Measurement of surface temperature as an aid to the diagnosis of burn depth.* Burns, 1991. 17(2): p. 123–7.; Mladick, R., N. Georgiade, and F. Thorne, *A clinical evaluation of the use of thermography in determining degree of burn injury.* Plastic & Reconstructive Surgery, 1966. 38(6): p. 512–8.; Lawson, R. W., G. Webster, D., *Thermographic Assessment of Burns and Frostbite.* Can. Med. Ass. J., 1961. 84: p. 1129.; Yamagami, S. and H. Yamagami, *Direct measurement of wound temperature during phacoemulsification.* Ophthalmologica, 1998. 212(1): p. 50–2.; Yamamoto, K. and S. Osako, *Temperature and humidity in the surgical wound cavity following tympanaplasty.* Jibiinkoka, 1966. 38(11): p. 1165–9.

For many variations of the invention, at least a portion of the inventive monitor is disposable or intended for one-time use. Instead of attempting sterilization, discarding such portions of the invention coming into contact with a patient may in many cases be preferred or the only reasonable option.

We claim:

1. A method of monitoring a wound area of a subject, said method comprising:

contacting a subject with a device comprising:

a support member, and one or more sensing portions supported by said support member, wherein said one or more sensing portions comprise at least one of: an impedance sensor and two temperature sensors;

obtaining measurement data from said one or more sensing portions, wherein said data is indicative of healing or infection of said wound area; and automatically initiating a secondary medical procedure in view of said obtained measurement data.

2. The method of claim 1, further comprising outputting a message indicative of said healing or said infection.

3. The method of claim 2, wherein said message is an audio message or visual message.

4. The method of claim 1, wherein said wound is a surgical wound.

5. The method of claim 1, wherein contacting comprises implanting at least a portion of said device within the body of said subject.

6. The method of claim 1, wherein at least a portion of said device is contacted with a skin surface of said subject.

7. The method of claim 1, wherein said data is indicative of healing.

8. The method of claim 1, wherein said data is indicative of infection.

9. The method of claim 1, wherein said device comprises an impedance sensor.

10. The method of claim 9, wherein said contacting comprises positioning a part of said impedance sensor adjacent a first side of a wound of said subject and positioning a part of said impedance sensor adjacent a second side of said wound.

11. The method of claim 1, further comprising electronic hardware that includes a memory unit and said method further comprises storing said obtained measurement data in said memory unit.

12. The method of claim 1, wherein said obtained measurement data comprises temperature measurement data.

13. The method of claim 12, wherein a decrease in temperature over time is indicative of wound healing.

14. The method of claim 12, wherein an increase in temperature over time is indicative of a wound infection.

15. A method of monitoring a wound area of a subject, said method comprising:
  contacting a subject with a device comprising:
    a support member, and
    first and second temperature sensors supported by said support member,
  wherein said contacting comprises positioning said first temperature sensor adjacent a non-wound area of said subject and positioning said second temperature sensor adjacent a wound area of said subject; and
  obtaining measurement data from said first and second temperature sensors, wherein said data is indicative of healing or infection of said wound area.

16. The method of claim 15, further comprising outputting a message indicative of said healing or said infection.

17. The method of claim 16, wherein said message is an audio message or visual message.

18. The method of claim 15, wherein said wound is a surgical wound.

19. The method of claim 15, wherein contacting comprises implanting at least a portion of said device within the body of said subject.

20. The method of claim 15, wherein at least a portion of said device is contacted with a skin surface of said subject.

21. The method of claim 15, wherein said data is indicative of healing.

22. The method of claim 21, wherein a decrease in temperature over time is indicative of wound healing.

23. The method of claim 15, wherein said data is indicative of infection.

24. The method of claim 23, wherein an increase in temperature over time is indicative of a wound infection.

25. The method of claim 15, wherein said device comprises an impedance sensor.

26. The method of claim 25, wherein said contacting comprises positioning a part of said impedance sensor adjacent a first side of a wound of said subject and positioning a part of said impedance sensor adjacent a second side of said wound.

27. The method of claim 15, further comprising electronic hardware that includes a memory unit and said method further comprises storing said obtained measurement data in said memory unit.

28. The method of claim 15, wherein said determining comprises analyzing said obtained measurement data using a programmed processor.

29. A method of monitoring a wound area of a subject, said method comprising:
  contacting a subject with a device comprising:
    a support member, and
    an impedance sensor and two temperature sensors supported by said support member, and
  obtaining measurement data from said impedance sensor and two temperature sensor, wherein said data is indicative of healing or infection of said wound area.

30. The method of claim 29, further comprising outputting a message indicative of said healing or said infection.

31. The method of claim 30, wherein said message is an audio message or visual message.

32. The method of claim 29, wherein said wound is a surgical wound.

33. The method of claim 29, wherein contacting comprises implanting at least a portion of said device within the body of said subject.

34. The method of claim 29, wherein at least a portion of said device is contacted with a skin surface of said subject.

35. The method of claim 29, wherein said data is indicative of healing.

36. The method of claim 35, wherein a decrease in temperature over time is indicative of wound healing.

37. The method of claim 29, wherein said data is indicative of infection.

38. The method of claim 37, wherein an increase in temperature over time is indicative of a wound infection.

39. The method of claim 29, wherein said contacting comprises positioning a part of said impedance sensor adjacent a first side of a wound of said subject and positioning a part of said impedance sensor adjacent a second side of said wound.

40. The method of claim 29, further comprising electronic hardware that includes a memory unit and said method further comprises storing said obtained measurement data in said memory unit.

41. The method of claim 29, wherein said determining comprises analyzing said obtained measurement data using a programmed processor.

* * * * *